United States Patent
Carlson et al.

(10) Patent No.: US 8,162,844 B2
(45) Date of Patent: Apr. 24, 2012

(54) MANAGING PRELOAD RESERVE BY TRACKING THE VENTRICULAR OPERATING POINT WITH HEART SOUNDS

(75) Inventors: Gerrard M. Carlson, Champlin, MN (US); Ramesh Wariar, Blaine, MN (US); Krzysztof Z. Siejko, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 428 days.

(21) Appl. No.: 12/547,207

(22) Filed: Aug. 25, 2009

(65) Prior Publication Data

US 2009/0312659 A1 Dec. 17, 2009

Related U.S. Application Data

(62) Division of application No. 11/189,462, filed on Jul. 26, 2005, now Pat. No. 7,585,279.

(51) Int. Cl.
*A61B 5/021* (2006.01)
*A61B 5/0225* (2006.01)
(52) U.S. Cl. .................. 600/528; 600/483; 600/514
(58) Field of Classification Search ............. 600/483, 600/514, 528
See application file for complete search history.

(56) References Cited

U.S. PATENT DOCUMENTS

| | | | |
|---|---|---|---|
| 4,094,308 A | 6/1978 | Cormier | |
| 4,289,141 A | 9/1981 | Cormier | |
| 4,446,872 A | 5/1984 | Marsoner et al. | |
| 4,548,204 A | 10/1985 | Groch et al. | |
| 4,649,930 A | 3/1987 | Groch et al. | |
| 4,763,646 A | 8/1988 | Lekholm | |
| 4,905,706 A | 3/1990 | Duff et al. | |
| 4,915,113 A | 4/1990 | Holman | |
| 4,989,611 A | 2/1991 | Zanetti et al. | |
| 5,159,932 A | 11/1992 | Zanetti et al. | |
| 5,365,932 A | 11/1994 | Greenhut | |
| 5,496,361 A | 3/1996 | Moberg et al. | |
| 5,554,177 A | 9/1996 | Kieval et al. | |
| 5,564,434 A | 10/1996 | Halperin et al. | |
| 5,674,256 A | 10/1997 | Carlson | |
| 5,685,317 A | 11/1997 | Sjostrom | |
| 5,687,738 A | 11/1997 | Shapiro et al. | |
| 5,697,375 A | 12/1997 | Hickey | |
| 5,700,283 A | 12/1997 | Salo | |
| 5,836,987 A | 11/1998 | Baumann et al. | |

(Continued)

OTHER PUBLICATIONS

"U.S. Appl. No. 11/189,462, Response filed Dec. 8, 2008 to Non Final Office Action mailed Sep. 8, 2008", 10 pgs.

(Continued)

*Primary Examiner* — Carl H. Layno
*Assistant Examiner* — Tammie K. Heller
(74) *Attorney, Agent, or Firm* — Schwegman, Lundberg & Woessner, P.A.

(57) ABSTRACT

A system and method for managing preload reserve and tracking the inotropic state of a patient's heart. The S1 heart sound is measured as a proxy for direct measurement of stroke volume. The S3 heart sound may be measured as a proxy for direct measurement of preload level. The S1-S3 pair yield a point on a Frank Starling type of curve, and reveal information regarding the patient's ventricular operating point and inotropic state. As an alternative, or in addition to, measurement of the S3 heart sound, the S4 heart sound may be measured or a direct pressure measurement may be made for the sake of determining the patient's preload level. The aforementioned measurements may be made by a cardiac rhythm management device, such as a pacemaker or implantable defibrillator.

20 Claims, 8 Drawing Sheets

U.S. PATENT DOCUMENTS

| | | |
|---|---|---|
| 5,991,661 A | 11/1999 | Park et al. |
| 6,044,298 A | 3/2000 | Salo et al. |
| 6,044,299 A | 3/2000 | Nilsson |
| 6,045,513 A | 4/2000 | Stone et al. |
| 6,053,872 A | 4/2000 | Mohler |
| 6,058,329 A | 5/2000 | Salo et al. |
| 6,064,910 A | 5/2000 | Andersson et al. |
| 6,077,227 A | 6/2000 | Miesel |
| 6,152,884 A | 11/2000 | Bjorgaas |
| 6,264,611 B1 | 7/2001 | Ishikawa et al. |
| 6,298,269 B1 | 10/2001 | Sweeney |
| 6,312,378 B1 | 11/2001 | Bardy |
| 6,366,811 B1 | 4/2002 | Carlson |
| 6,368,283 B1 | 4/2002 | Xu et al. |
| 6,409,675 B1 | 6/2002 | Turcott |
| 6,415,033 B1 | 7/2002 | Halleck et al. |
| 6,440,082 B1 | 8/2002 | Joo et al. |
| 6,477,406 B1 | 11/2002 | Turcott |
| 6,527,729 B1 | 3/2003 | Turcott |
| 6,575,916 B2 | 6/2003 | Halleck et al. |
| 6,643,548 B1 | 11/2003 | Mai et al. |
| 6,650,940 B1 | 11/2003 | Zhu et al. |
| 6,665,564 B2 | 12/2003 | Lincoln et al. |
| 6,795,732 B2 | 9/2004 | Stadler et al. |
| 6,810,287 B2 | 10/2004 | Zhu et al. |
| 6,824,519 B2 | 11/2004 | Narimatsu et al. |
| 6,830,548 B2 | 12/2004 | Bonnet et al. |
| 6,845,263 B2 | 1/2005 | Kawaguchi |
| 7,115,096 B2 | 10/2006 | Siejko et al. |
| 7,174,203 B2 | 2/2007 | Arand et al. |
| 7,585,279 B2 | 9/2009 | Carlson et al. |
| 2002/0001390 A1 | 1/2002 | Kawaguchi |
| 2002/0035337 A1 | 3/2002 | Oka |
| 2002/0082645 A1 | 6/2002 | Sweeney |
| 2002/0107450 A1 | 8/2002 | Ogura |
| 2002/0147401 A1 | 10/2002 | Oka |
| 2002/0151812 A1 | 10/2002 | Scheiner et al. |
| 2002/0151938 A1 | 10/2002 | Corbucci |
| 2003/0055352 A1 | 3/2003 | Hayek et al. |
| 2003/0069608 A1 | 4/2003 | Sweeney |
| 2003/0072458 A1 | 4/2003 | Halleck et al. |
| 2003/0093002 A1 | 5/2003 | Kuo |
| 2003/0093003 A1 | 5/2003 | Watrous et al. |
| 2003/0120159 A1 | 6/2003 | Mohler |
| 2003/0176896 A1 | 9/2003 | Lincoln et al. |
| 2003/0208240 A1 | 11/2003 | Pastore et al. |
| 2003/0216620 A1 | 11/2003 | Jain et al. |
| 2003/0229289 A1 | 12/2003 | Mohler |
| 2004/0024423 A1 | 2/2004 | Lincoln et al. |
| 2004/0039419 A1 | 2/2004 | Stickney et al. |
| 2004/0039420 A1 | 2/2004 | Jayne et al. |
| 2004/0064056 A1 | 4/2004 | Ogura |
| 2004/0078059 A1 | 4/2004 | Ding et al. |
| 2004/0078060 A1 | 4/2004 | Ding et al. |
| 2004/0106960 A1 | 6/2004 | Siejko et al. |
| 2004/0106961 A1 | 6/2004 | Siejko et al. |
| 2004/0127792 A1 | 7/2004 | Siejko et al. |
| 2004/0138572 A1 | 7/2004 | Thiagarajan |
| 2004/0167417 A1 | 8/2004 | Schulhauser et al. |
| 2004/0215264 A1 | 10/2004 | Van Bentem |
| 2004/0225332 A1 | 11/2004 | Gebhardt et al. |
| 2004/0236239 A1 | 11/2004 | Murray et al. |
| 2004/0254481 A1 | 12/2004 | Brodnick |
| 2004/0267147 A1 | 12/2004 | Sullivan |
| 2004/0267148 A1 | 12/2004 | Arand et al. |
| 2005/0027323 A1 | 2/2005 | Mulligan et al. |
| 2005/0033190 A1 | 2/2005 | Bauer |
| 2005/0148896 A1 | 7/2005 | Siejko et al. |
| 2006/0167358 A1 | 7/2006 | Karamanoglu et al. |
| 2006/0282000 A1 | 12/2006 | Zhang et al. |
| 2007/0027400 A1 | 2/2007 | Carlson et al. |

OTHER PUBLICATIONS

"U.S. Appl. No. 11/189,462, Response filed Feb. 24, 2009 to Final Office Action mailed Jan. 15, 2009", 11 pgs.

"U.S. Appl. No. 11/189,462, Non-Final Office Action mailed Sep. 8, 2008.", 9 pgs.

"U.S. Appl. No. 11/189,462, Final Office Action mailed Jan. 15, 2009", 9 pgs.

Little, W. C, et al., "Assessment of Normal and Abnormal Cardiac Function", *Heart Disease: A Textbook of Cardiovascular Medicine*, W.B. Saunders, Philadelphia PA, (2001), 479-502.

"U.S. Appl. No. 11/189,462, Notice of Allowance mailed May 5, 2009", 9 pgs.

"U.S. Appl. No. 11/189,462, Preliminary Amendment and Response filed Jul. 7, 2008 to Restriction Requirement mailed Jun. 6, 2008", 8 pgs.

"U.S. Appl. No. 11/189,462, Restriction Requirement mailed Jun. 6, 2008", 12 pgs.

MANAGING PRELOAD RESERVE BY TRACKING THE VENTRICULAR OPERATING POINT WITH HEART SOUNDS

CROSS REFERENCE TO RELATED APPLICATION

This application is a divisional of U.S. application Ser. No. 11/189,462, filed Jul. 26, 2005, now U.S. Pat. No. 7,585,279, which is hereby incorporated by reference in its entirety.

TECHNICAL FIELD

The present document relates to cardiac rhythm management devices generally, and more particularly to cardiac rhythm management devices that monitor the inotropic state exhibited by a heart, detect changes in the inotropic state, and identify the particular operating point exhibited by a heart.

BACKGROUND

Heart failure is a condition wherein the heart fails to circulate blood sufficiently to meet the metabolic demands of the various tissues of the body. In other words, cardiac output is insufficient to satisfy the body.

Cardiac output is influenced by the stroke volume exhibited by the heart. For a given heart, stroke volume may be considered a function of preload and inotropic state. Briefly, preload refers to the stretching of the myocardial cells in a chamber (e.g., left ventricle) during diastole, before contraction of the chamber. Preload may be measured as the end-diastolic volume or pressure exhibited by the blood within the chamber in question. Inotropic state refers generally to the hormonal milieu exerting influence upon the heart. The inotropic state of a heart determines the strength of its next contraction.

A Frank Starling curve presents the relationship between stroke volume, preload, and inotropic state for a given heart. An exemplary Frank Starling curve is depicted in FIG. 1. The chart of FIG. 1 is plotted on a Cartesian plane, with stroke volume measured along the y-axis, and preload measured along the x-axis. Three solid curves 100, 102, and 104 are depicted on the chart. Each curve 100, 102, and 104 corresponds to a different inotropic state. Curve 100 corresponds to inotropic state $S_1$, curve 102 corresponds to inotropic state $S_2$, and curve 104 corresponds to inotropic state $S_3$.

The inotropic state exhibited by a person's heart may vary with exertion or emotional state, among other factors. Thus, for example, inotropic state S1 (curve 100) may represent the inotropic state of a particular person's heart during ordinary waking non-strenuous activity. State S2 (curve 102) may represent the inotropic state of the person's heart during strenuous exertion, and state S3 (curve 104) may represent the inotropic state of the person's heart during rest. As can be seen from FIG. 1, when the inotropic state exhibited by a heart elevates, a greater stroke volume is yielded for a given level of preload (because the hormonal influences upon the heart cause the heart to contract more forcefully). Conversely, when the inotropic state exhibited by a heart depresses, a lesser stroke volume is yielded for a given level of preload.

SUMMARY

As can be seen in FIG. 1, the stroke volume-preload curve for a given inotropic state is generally a monotonic, increasing curve. Therefore, stroke volume may be elevated by elevating a patient's preload. However, as can also be seen from FIG. 1, the stroke volume-preload curve for an inotropic state tends to level off (exhibit only a slight positive derivative) after a particular level of preload, referred to as the "critical preload."

For a given inotropic state, elevating a patient's preload beyond the critical preload is generally not an effective strategy for increasing stroke volume, and may lead to pulmonary congestion. Briefly, an elevation in preload corresponds to an elevation in end-diastolic pressure exhibited by the blood in, for example, the left ventricle. Elevated pressure in the left ventricle leads to elevated pressure in the left atrium, which, in turn, leads to elevated pressure in the veins of the lungs. If the pressure in the veins of the lungs exceeds a given point, plasma leaves the circulation space of the lungs and enters into the intercellular space therein. This condition, referred to as "pulmonary congestion," interferes with the oxygen exchange function of the lungs, and leaves the patient short of breath.

A patient with heart failure generally exhibits a stroke volume-preload curve that is depressed. An exemplary curve 106 typical of heart failure is shown in FIG. 1. The curve 106 reveals that the patient's heart produces little stroke volume. One strategy for dealing with such a patient is to elevate the patient's preload (e.g., administer intravenous fluids or administer salt), so that the patient's stroke volume will rise. However, as discussed above, such a strategy should not be pursued to the point of elevating the preload beyond the critical preload. To achieve gains in stroke volume beyond what may be achieved by elevation of preload, the patient's inotropic state may be elevated (e.g., by administration of an inotrope, for example). By practicing a two-pronged approach of elevating both preload and inotropic state, a heart failure patient may attain a satisfactory stroke volume, while reducing the risk of pulmonary congestion.

The foregoing discussion reveals the desirability of a device and/or system for monitoring a patient's preload, stroke volume, and inotropic state. It is particularly desirable to achieve such an end with the use of existing technology, thereby requiring minimal risk and investment. Against this backdrop, the present invention was developed. According to one embodiment of the present invention, a method includes monitoring an S1 heart sound emitted by a heart of a patient. The method also includes monitoring a proxy variable indicating preload exhibited by the heart. Finally, it is determined whether the heart has exhibited an inotropic state change, using at least the S1 heart sound and the proxy variable.

According to another embodiment of the present invention, a method includes sensing a plurality of S3 or S4 heart sounds emitted by a heart of a patient, each of which is represented as a time-varying signal with at least one maxima and minima. The method also includes finding a greatest difference between a minima and maxima that are consecutive for each of the time-varying signals representing the plurality of S3 or S4 heart sounds, thereby yielding a set of peak-to-peak differences. Finally, the inotropic state of the heart is monitored, using the set of peak-to-peak differences and an indicator of stroke volume.

According to yet another embodiment of the present invention, a system includes a preload altering device, and an implantable device. The implantable device includes a transducer. The implantable device also includes a control circuit coupled to the transducer. The control circuit is configured to cooperate with the transducer to monitor an S1 heart sound emitted by a heart of a patient, monitor a proxy variable indicating preload exhibited by the heart, and communicate a control signal to the preload altering device.

According to yet another embodiment of the present invention, a system includes an inotropic state altering device and an implantable device. The implantable device includes a transducer and a control circuit coupled to the transducer. The control circuit is configured to cooperate with the transducer to monitor an S1 heart sound emitted by a heart of a patient, monitor a proxy variable indicating preload exhibited by the heart, and communicate a control signal to the inotropic state altering device using the inotropic state.

According to yet another embodiment of the present invention, a device includes a transducer and a control circuit coupled to the transducer. The control circuit is configured to cooperate with the transducer to monitor an S1 heart sound emitted by a heart of a patient, and monitor a proxy variable indicating preload exhibited by the heart.

DETAILED DESCRIPTION

By way of brief background, the heart circulates blood through a known sequence of cardiac chamber contractions, relaxations, and valve manipulations. The heart makes certain sounds as it progresses through a cardiac cycle, which are caused by the circulation of the blood and the opening and closing of various heart valves. These heart sounds occur in a characteristic sequence in a cardiac cycle, and are respectively referred to as S1, S2, S3 and S4.

The S1 heart sound is caused by acceleration and deceleration of blood, and closure of the mitral and tricuspid valves. The S1 heart sound generated during a given cardiac cycle exhibits morphological characteristics (e.g., median peak-to-peak amplitude of a set of S1 heart sounds) are indicative of the maximum rate of change of pressure in the left ventricle during the given cardiac cycle. S2 is believed to be indicative of, among other things, aortic valve closure and pulmonary valve closure. S3 is known to be a ventricular diastolic filling sound often indicative of certain pathological conditions including heart failure. S4 is believed to be a ventricular diastolic filling sound resulted from atrial contraction and is usually indicative of pathological conditions.

Figure 2A:
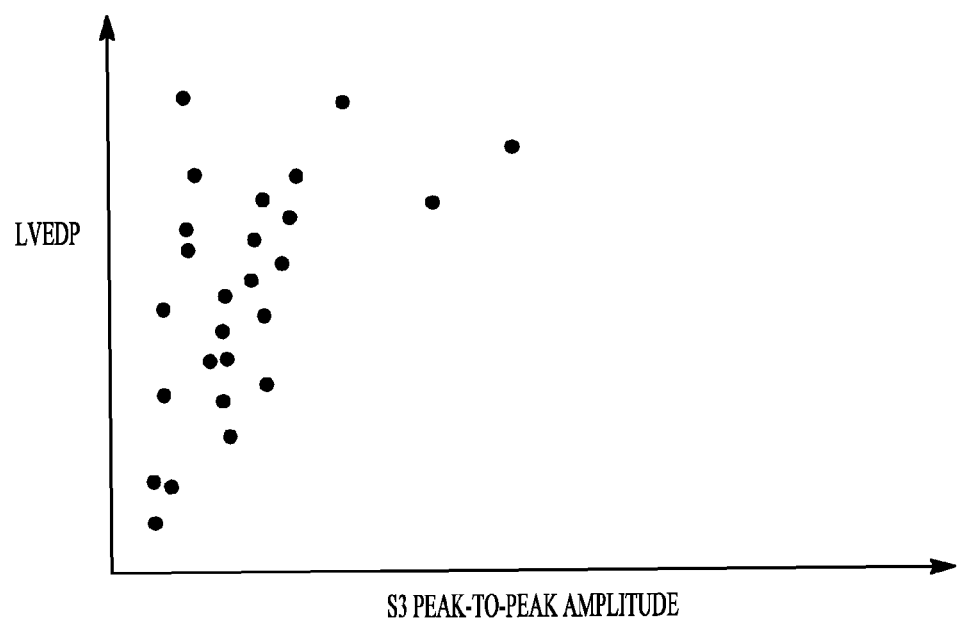
FIG. 2A depicts a scatter graph that relates left ventricular end-diastolic pressure (LVEDP) to the maximum peak-to-peak amplitude exhibited by the third heart sound.

FIG. 2A depicts a scatter graph that relates left ventricular end-diastolic pressure (LVEDP) to the maximum peak-to-peak amplitude exhibited by the third heart sound (referred to as "S3"). The chart of FIG. 2A is a Cartesian plane, with left ventricular end-diastolic pressure measured along the y-axis, and maximum peak-to-peak S3 amplitude measured along the x-axis.

Each point on the Cartesian plane represents data taken from an individual patient. For each patient, a pressure sensor was introduced into the patient's left ventricle, thereby enabling direct measurement of left ventricular end-diastolic pressure. Additionally, a pacemaker having an internal accelerometer was placed upon each patient's chest. (As used herein, the term "pacemaker" refers generally to any implantable cardiac rhythm management device, and includes within its meaning cardiac pacemakers, implantable defibrillators, cardiac resynchronization therapy (CRT) devices, implantable defibrillators having pacing and/or CRT capabilities, and pacemakers having CRT capabilities). For each of a set of N heartbeats, the patient's left ventricular end-diastolic pressure was directly measured, and the maximum peak-to-peak S3 amplitude observed by the accelerometer in the pacemaker was recorded. After obtaining the data for a given patient, the pressure measurements were averaged, resulting in an average left ventricular end-diastolic pressure exhibited by a given patient. Also, for a given patient, the median value of the N maximum peak-to-peak S3 measurements was found, yielding a median maximum peak-to-peak S3 amplitude exhibited by a given patient. The Cartesian plane of FIG. 2 was constructed by plotting the average left ventricular end-diastolic pressure exhibited by a given patient against the median maximum peak-to-peak S3 amplitude exhibited by a given patient.

As can be seen from FIG. 2A, a generally linear relationship exists between left ventricular end-diastolic pressure and maximum peak-to-peak S3 amplitude. Therefore, maximum peak-to-peak S3 amplitude (or a median of multiple such measurements) may be used as a proxy for direct measurement of left ventricular end-diastolic pressure (i.e., preload).

Figure 2B:
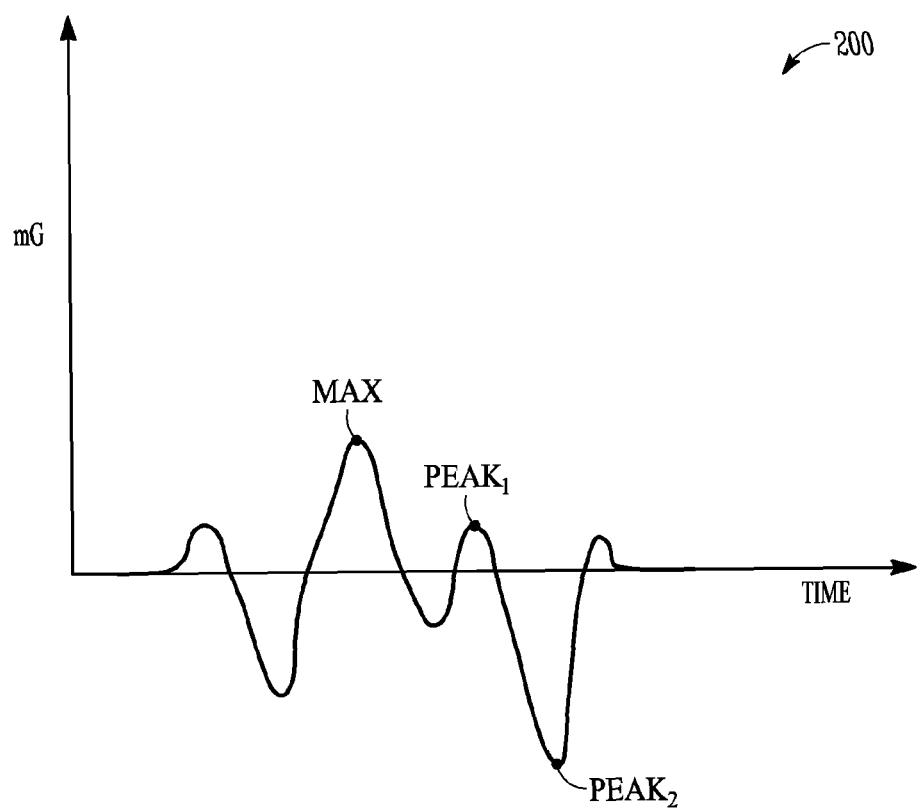
FIG. 2B depicts an exemplary isolated S3 heart sound 200, as observed via an accelerometer located within a pacemaker implanted in a patient.

FIG. 2B presents an exemplary isolated S3 heart sound 200, as observed via an accelerometer located within a pacemaker implanted in a patient. The S3 heart sound 200 of FIG. 2 includes seven peaks. To find the maximum peak-to-peak value exhibited by the S3 heart sound, one may use various alternatives. For example, one may find the difference between the greatest positive-going peak (identified by the label "Max") and the greatest negative-going peak (identified by the label "Peak$_2$"). Thus, the difference in amplitude between Max and Peak$_2$ may represent the maximum peak-to-peak value of the S3 heart sound. Thereafter, the median of a populace of such amplitudes is found, in order to arrive at a median peak-to-peak amplitude. Alternatively, one may find the greatest difference in consecutive peaks. Thus, for example, the difference between Peak$_1$ and Peak$_2$ may represent the maximum peak-to-peak value of the S3 heart sound 200. Again, the median or other central tendency of a populace of such amplitudes may be found, in order to arrive at a median or like peak-to-peak amplitude.

The inventors have discovered, among other things, that calculating the maximum peak-to-peak value of an S3 heart sound according to the latter method results in better correlation to left ventricular end-diastolic pressure. Nevertheless, both alternatives and the like are within the scope of the present invention.

In addition to the methods of finding a median peak-to-peak amplitude of an S3 (or other) heart sound just as described, the following method may also be employed. One may first find the median maximum peak exhibited by a populace of S3 (or S1 or other) heart sounds, and may also find the median minimum peak exhibited by the same populace of S3 (or S1 or other) heart sounds. Then, the difference between the two medians may be found, thereby arriving at the median peak-to-peak amplitude for a populace of heart sounds.

The S1 heart sound relates to contractility, which, in turn, relates to stroke volume. For example, the median peak-to-peak amplitude of an S1 heart sound relates to contractility. The median peak-to-peak amplitude of a set of S1 heart sounds may be found according to the aforementioned methods.

Figure 1:
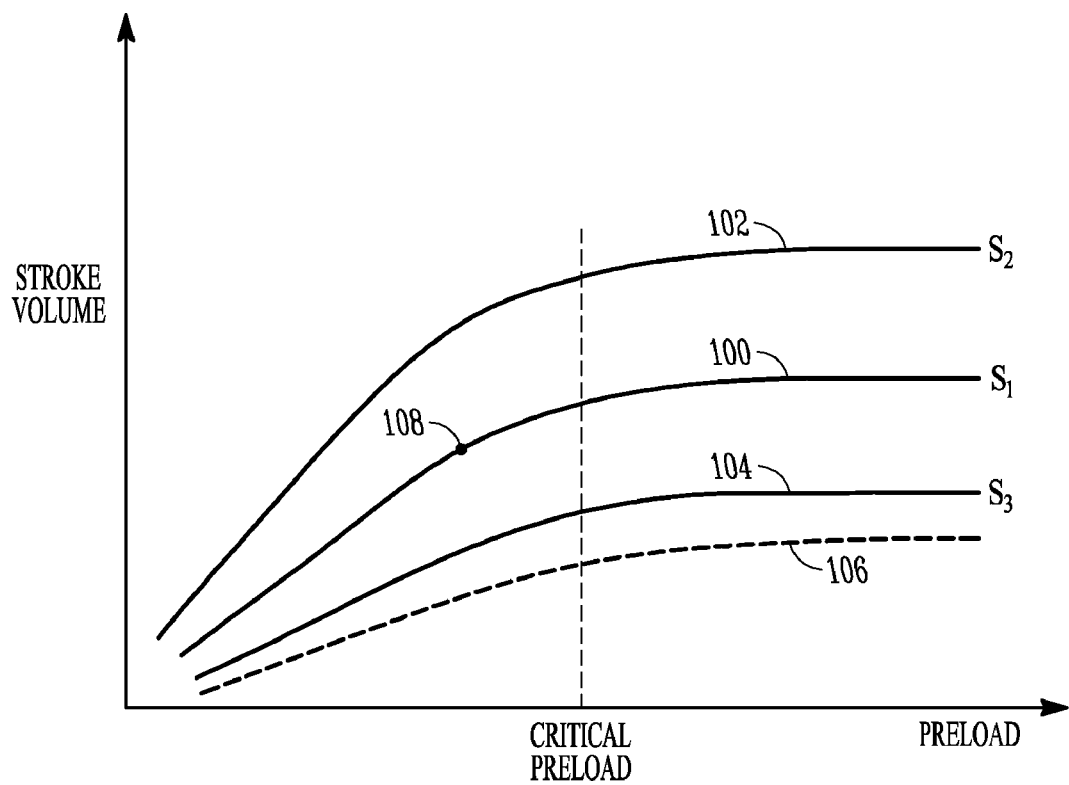
FIG. 1 depicts an exemplary Frank Starling curve.

Because the S3 heart sound may be measured as a proxy for direct measurement of preload, and because the S1 heart sound may be measured as a proxy for measurement of stroke volume, a point on a Frank Starling type of curve may be determined indirectly via detection of heart sounds. Thus, for example, the point 108 on the Frank Starling curve of FIG. 1 may be approximated by measurement of the S3 heart sound to determine the point's 108 x-coordinate, and by measurement of the S1 heart sound to determine the point's 108 y-coordinate.

Figure 3:
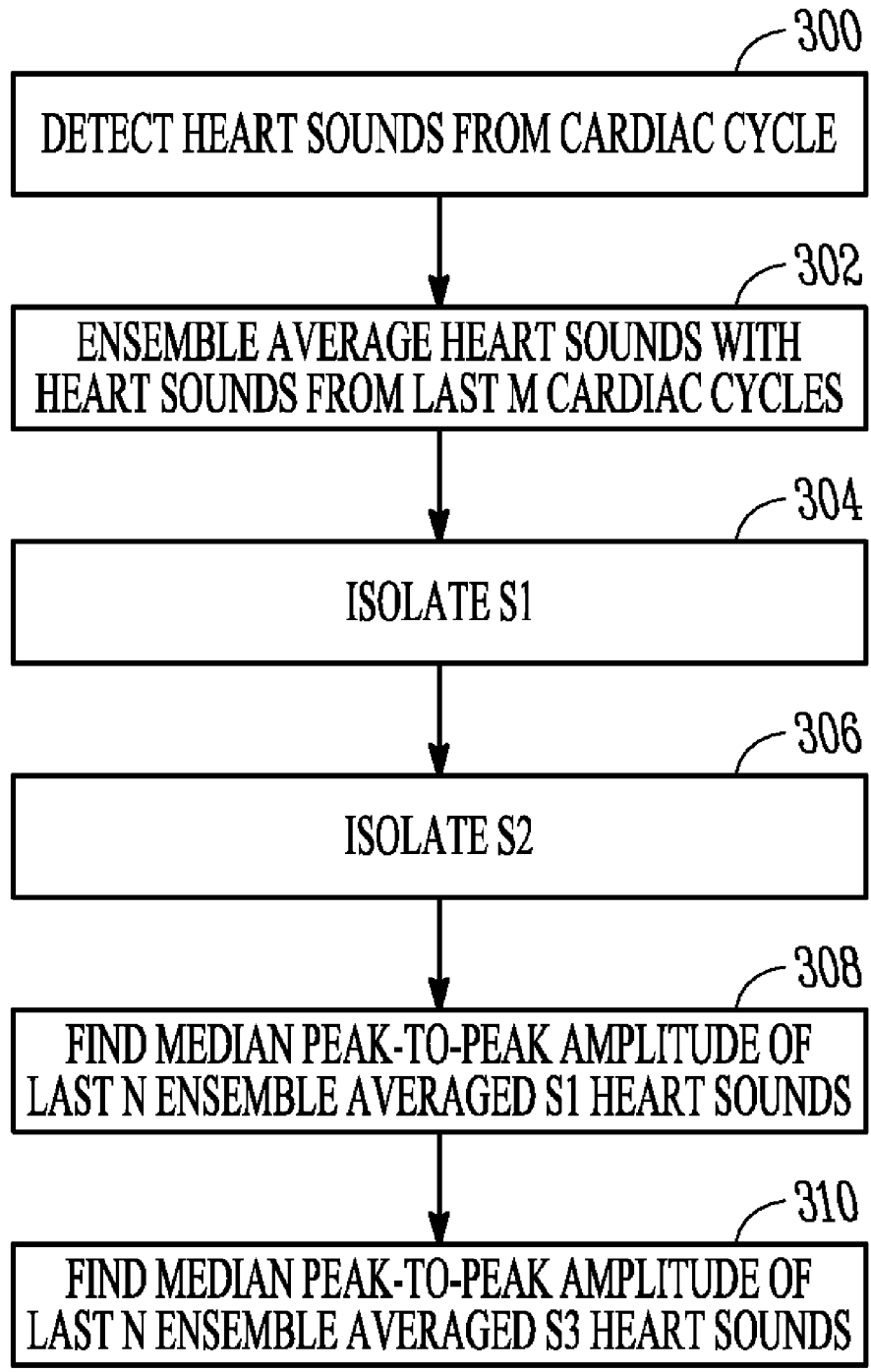
FIG. 3 depicts a method by which a point on a Frank Starling type of curve may be determined, according to an embodiment of the present invention.

FIG. 3 depicts a method by which a point on a Frank Starling type of curve may be determined. As discussed below, variations of the method of FIG. 3 exist. The method of FIG. 3 begins by detecting the various sounds (S1, S2, etc.) emitted during a cardiac cycle, as shown in operation 300. Next, the heart sounds detected in operation 300 may be ensemble averaged with the heart sounds detected over the last M cardiac cycles, as shown in operation 302. M may be an integer greater than or equal to one. If M is equal to one, then no ensemble averaging occurs, and a single heart sound is instead used to obtain the desired information. The particular value assigned to M is a design choice influenced by, amongst other factors, the noise content of the heart sound signal. After execution of operation 302, the S1 heart sound is isolated from the ensemble-averaged signal (operation 304). Also, the S3 heart sound is isolated therefrom (operation 306).

The median peak-to-peak amplitudes of the last N ensemble-averaged S1 and S3 heart sounds are then determined (operations 308 and 310, respectively). N may be any positive number greater than or equal to one. In one embodiment, N may be assigned a value equal to M (see operation 302). The median peak-to-peak amplitudes determined during operation 308 and 310 may be found according to any of the methods discussed with reference to FIG. 2B.

Figure 4:
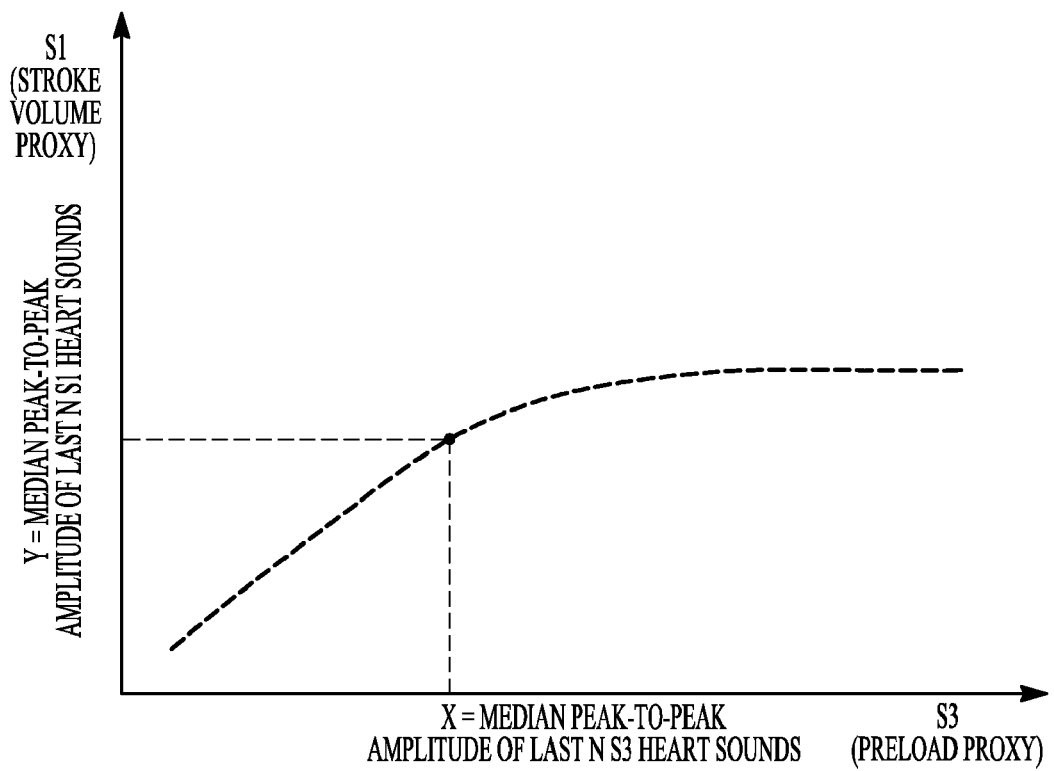
FIG. 4 depicts a Frank Starling type of curve, according to an aspect of the present invention.

The method of FIG. 3 may be used to find a point on a Frank Starling type of curve, as shown in FIG. 4. As can be seen from FIG. 4, the median peak-to-peak amplitude exhibited by a set of N S3 sounds is used to determine an x-coordinate of a point on a Frank Starling type of curve, and the median peak-to-peak amplitude exhibited by a set of N S1 heart sounds is to determine a y-coordinate.

The method of FIG. 3 may be modified to make use of other proxies for preload. For example, there exists a relationship between the S4 heart sound and the stiffness of the left ventricle during the active filling period. Therefore, the method of FIG. 3 may be modified to take account of the S4 heart sound, either as a replacement for, or in addition to, the S3 heart sound. For example, the span of time between the P wave and the origination of the S4 heart sound reveals information about preload: the shorter the span of time, the greater the pressure. Thus, for example, the method of FIG. 3 may be modified to find the median of the reciprocal of the span of time between the P wave and the origination of the S4 heart sound for a set of N cardiac cycles. The aforementioned median may be used to determine the x-coordinate of the point on the Frank Starling curve. In addition, the method of FIG. 3 may be modified to find the median peak-to-peak amplitude exhibited by the S4 heart sound, instead of (or in addition to) the median peak-to-peak amplitude exhibited by the S3 heart sound. Still further, the method of FIG. 3 may be modified to utilize a direct pressure measurement obtained by a pressure sensor (such as may be introduced into the right ventricle or pulmonary artery, for example). Thus, a median value pressure exhibited over a set of N cardiac cycles may be used to determine the x-coordinate.

The method of FIG. 3, or any of its aforementioned variations, may be used as a means by which to determine whether a patient's inotropic state has changed. Such a determination may be useful, for example, in determining an appropriate therapy such as the proper dosing of an inotrope or other substance for a given patient. An exemplary method is depicted in FIG. 5.

Figure 5:
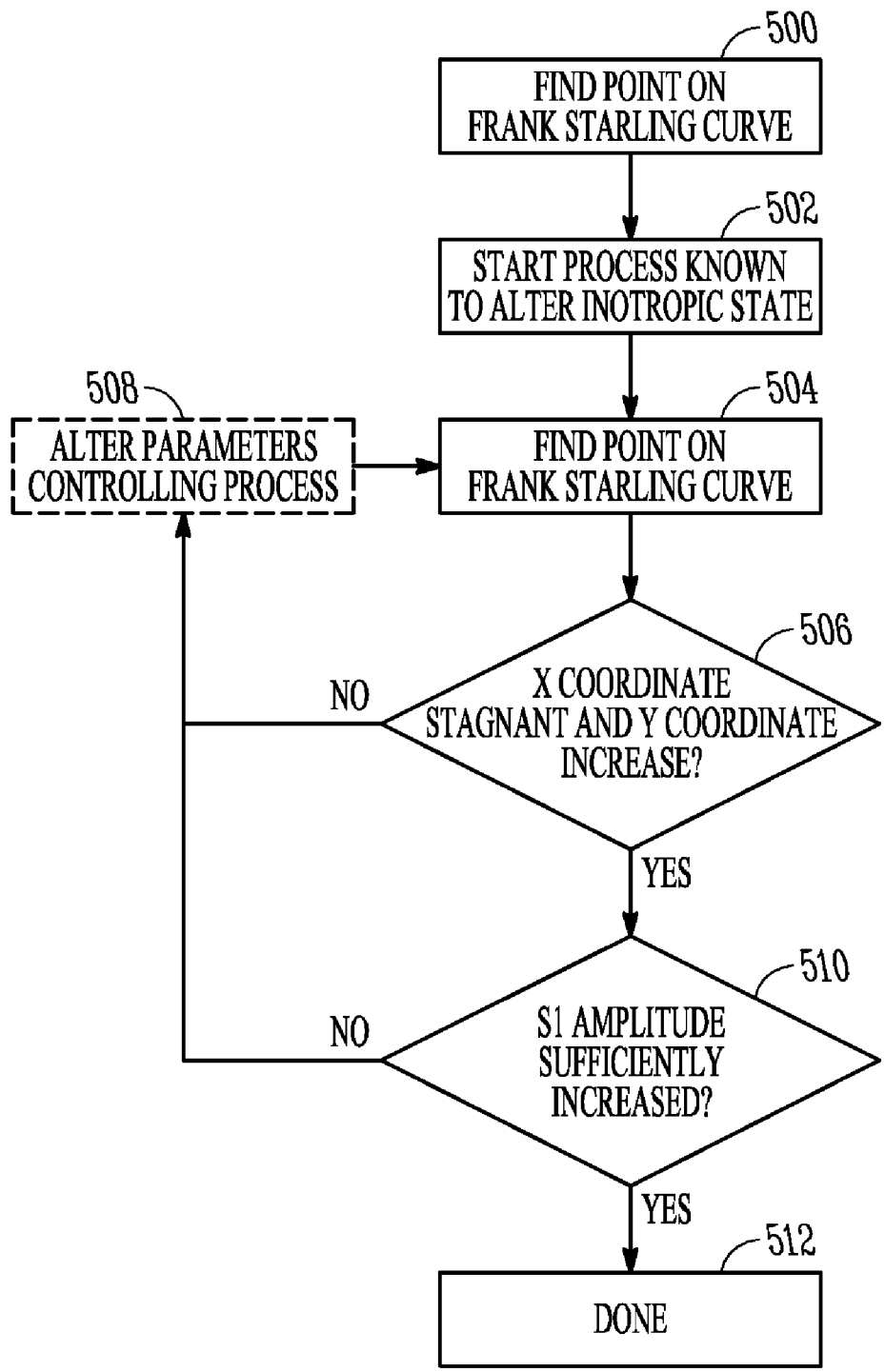
FIG. 5 depicts an exemplary method for controlling the alteration of a patient's inotropic state, according to an embodiment of the present invention.

The particular exemplary method depicted in FIG. 5 is useful, for example, in a setting in which an inotrope or other substance is being administered to a patient, in an effort to elevate the patient's inotropic state. Although the exemplary method of FIG. 5 determines whether a patient's inotropic state has been sufficiently elevated, the method of FIG. 5 may be altered to determine whether a patient's inotropic state has been sufficiently depressed, should such a determination be desired.

The method of FIG. 5 commences by determining a point on a Frank Starling type of curve, as shown in operation 500. Operation 500 may be effectuated by execution of the method of FIG. 3 or any of its variations. After execution of operation 500, an x and y coordinate describing the patient's inotropic state is known.

Next, as shown in operation 502, a process known to alter a person's inotropic state is commenced. For example, operation 502 may include administration of an inotrope to a patient, in order to elevate the patient's inotropic state. An inotrope may be administered by an intravenous drip apparatus, for example, or by another substance dispenser, which serve as an inotropic state altering device when so used. After initiation of the process of operation 502, the patient's x and y coordinates on the Frank Starling type of curve is once again found, as shown in operation 504. Thus, by virtue of execution of operations 500 and 504, a set of "before" and "after" points on a Frank Starling type of curve are determined for the patient.

In operation 506, two sets of coordinates for the patient are compared. In the context of an initial iteration through the process, the comparison occurs between the coordinates determined in operation 500 (i.e., the "before" coordinates) and the coordinates determined in operation 504 (i.e., the "after" coordinates). In the context of a subsequent iteration, the comparison occurs between a set of coordinates determined at one point in time and a most recent or other set of coordinates determined at an earlier point in time, with both points in time occurring after initiation of the process of operation 502. Turning to the comparison itself, if the comparison reveals that the x coordinate has not increased, but that the y coordinate has increased, then it may be inferred that the patient's inotropic state has been elevated.

If the patient's inotropic state has not been elevated, then control may be passed to operation 508. Operation 508 is optional. In operation 508, one or more parameters controlling the process are altered. For example, if the process of operation 502 includes applying cardiac resynchronization therapy (CRT) to the patient, then one or more parameters determining the CRT, such as the atrioventricular delay, may be altered in order to improve the process' ability to elevate the patient's inotropic state. Other examples of CRT control parameters include, without limitation, selecting which particular electrode(s) to use for delivering CRT electrical stimuli. If the nature of the process of operation 502 does not allow for alteration of a control parameter (e.g., administration or other delivery of an inotrope), operation 508 may be omitted altogether, meaning that the process merely continues on, until an elevation in inotropic state is observed.

If, on the other hand, the patient's inotropic state has been elevated, control is passed to operation 510, in which it is determined whether the patient's stroke volume (inferred from the y-coordinate) has been sufficiently increased. If not, control is returned to optional operation 508. If operation 508 has been omitted, then control is returned to operation 506. If it is determined that the patient's inotropic state has been sufficiently elevated given the medical goals associated with the patient, then control is passed to operation 512. In operation 512, the process of operation 502 may be terminated, if appropriate (e.g., administration of an inotrope), or the process may be permitted to carry on, if appropriate (e.g., execution of CRT therapy).

Earlier, it was stated that the method of FIG. 5 may be altered to determine whether a patient's inotropic state has been depressed. Such an alteration includes changing the comparison of operation 506 to identify an occurrence in which the x coordinate did not decrease, but the y coordinate decreased. Such an occurrence indicates depression of the patient's inotropic state. The alteration may also include modifying operation 510 to determine whether the patient's stroke volume (inferred from the y-coordinate) has been sufficiently decreased, given the medical goals associated with the patient.

Figure 6:
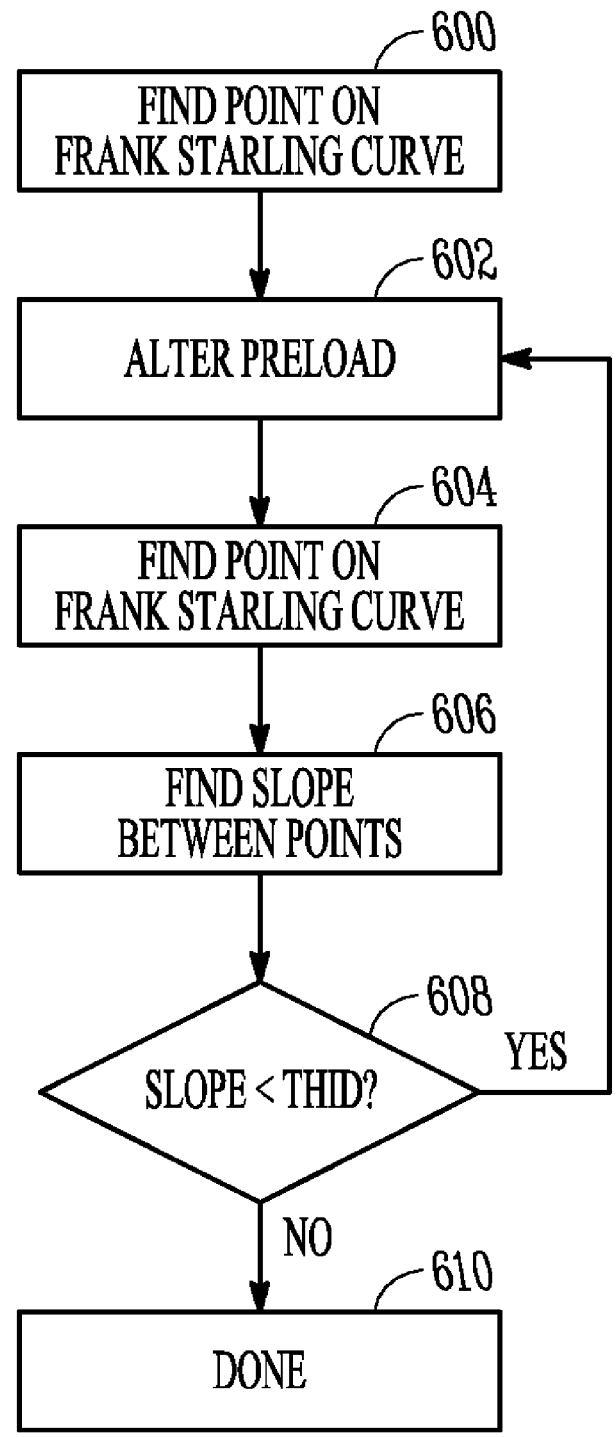
FIG. 6 depicts an exemplary method for determining whether a patient preload exceeds the critical preload, according to an embodiment of the present invention.

FIG. 6 depicts an exemplary method for determining whether a patient preload exceeds the critical preload. The method of FIG. 6 may be useful in a setting in which the patient's preload level is being adjusted. For example, a diuretic may be administered to a patient for the purpose of lowering the patient's preload level. A diuretic may be administered via an intravenous drip apparatus or other form of substance dispenser, for example, which serves as an example of a preload altering device when so used. The method of FIG. 6 may be used to determine that the patient's preload level has been brought beneath the critical preload. The method of FIG. 6 may be altered to detect a circumstance in which a patient's preload level has been elevated beyond the critical preload.

The method of FIG. 6 commences by determining a point on a Frank Starling type of curve, as shown in operation 600. Operation 600 may be effectuated by execution of the method of FIG. 3 or any of its variations. After execution of operation 600, an x and y coordinate describing the patient's inotropic state is known.

Next, as shown in operation 602, a process known to alter a person's preload level is commenced. For example, operation 602 may include administration of a diuretic to a patient, in order to reduce the patient's preload level. After initiation of the process of operation 602, the patient's x and y coordinates on the Frank Starling type of curve is once again found, as shown in operation 604. Thus, by virtue of execution of operations 600 and 604, a set of "before" and "after" points on a Frank Starling type of curve are determined for the patient.

In operation 606, the slope between two sets of coordinates for the patient is found. In the context of an initial iteration through the process, the slope is found between the coordinates determined in operation 600 (i.e., the "before" coordinates) and the coordinates determined in operation 604 (i.e., the "after" coordinates). In the context of a subsequent iteration, the slope is found between a set of coordinates determined at one point in time and a set of coordinates determined at a most recent or other earlier point in time, with both points in time occurring after initiation of the process of operation 602.

After finding the slope in operation 606, the slope is compared to a threshold, as depicted in operation 608. The threshold is chosen to be a value that approximately corresponds with the critical preload level on a Frank Starling curve. If the slope is less than the threshold, then the preload level is inferred to be beyond the critical preload level. In such a circumstance, control is returned to operation 602, meaning that the process of operation 602 continues (e.g., administration of a diuretic), and that another set of coordinates for the patient will be measured.

On the other hand, if the slope is greater than the threshold, it may be inferred that the patient's preload level is less than the critical preload level, in which case control is passed to operation 610. In operation 610, the process of operation 602 may be terminated, if appropriate. For example, if operation 602 included administration of a diuretic, then such administration may be halted by operation 610.

Figure 7:
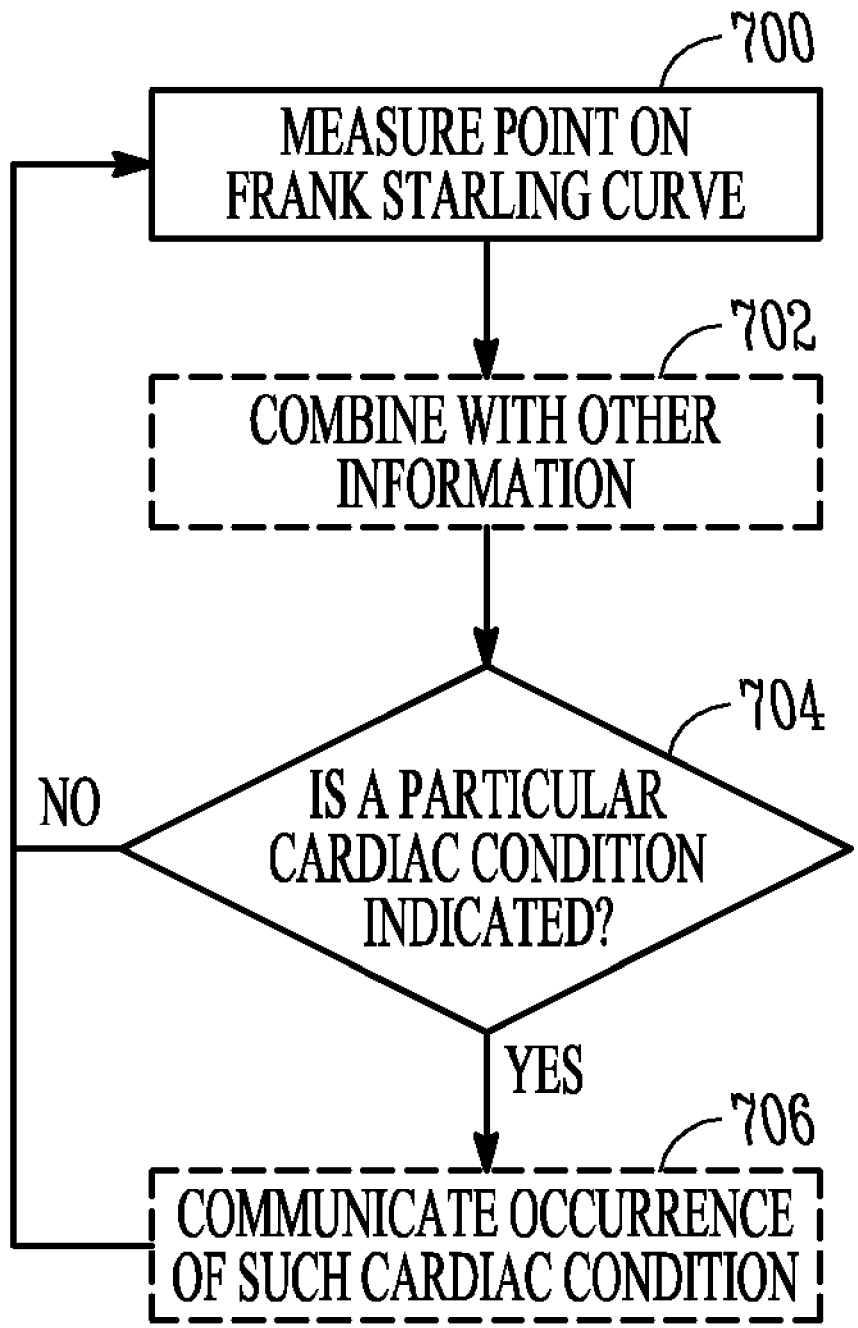
FIG. 7 depicts a method for determining whether a particular cardiac condition is indicated, according to an embodiment of the present invention.

FIG. 7 depicts a method for determining whether a particular cardiac condition (e.g., acute heart failure decompensation) is indicated. The method of FIG. 7 commences with measuring a point on a Frank Starling type of curve, as shown in operation 700. Operation 700 may use the method of FIG. 3 or any of its variations. After operation 700, an x and y coordinate describing the patient's inotropic state is known. After execution of operation 700, control is passed to operation 702.

Operation 702 is an optional operation, and may be omitted altogether. In operation 702, the x and y coordinate obtained in operation 700 are combined with other information. The other information accessed in operation 702 may include any information obtained by a pacemaker, such as activity level information, respiration rate information, posture information, or past x and y coordinate information.

Based upon the combination of information (or based solely upon the information from operation 700), it is determined whether a particular cardiac condition is indicated in operation 704. For example, by combining activity level and x and y coordinate information, it may be determined that a patient's heart exhibits an abnormally low stroke volume for a given preload and activity level. Accordingly, it may be inferred that the patient is exhibiting acute heart failure decompensation. If no particular cardiac condition is detected in operation 704, control returns to operation 700, and monitoring of the patient's preload and stroke volume proxies continues. On the other hand, if a particular cardiac condition is detected, control may pass to operation 706.

Operation 706 is optional. In operation 706, occurrence of the detected condition is communicated. The communication may occur between an implanted cardiac management device (performing operations 700-706) and a programmer, a personal digital assistant, an access point to a network, such as a wireless or wired network, or to a wireless communication device that may forward the message to an access point for communication to a remote computing system, for example. (The programmer or personal digital assistant may relay such a message to a remote computing system). Alternatively, the communication may occur between the detection routine executing on the internal controller and a history logging routine executed by the same internal controller. Thus, the occurrence of the detected condition is logged, so that a health care professional may become aware of the condition, for example, the next time he or she reads the data contained in the log. After execution of operation 706, control is returned to operation 700, and monitoring continues.

The method of FIG. 7 may be performed continually or repeatedly. For example, a patient may be monitored for a given cardiac condition once per day (e.g., at night) or several times each day, meaning that the method of FIG. 7 would be executed once per day or several times per day.

Figure 8:
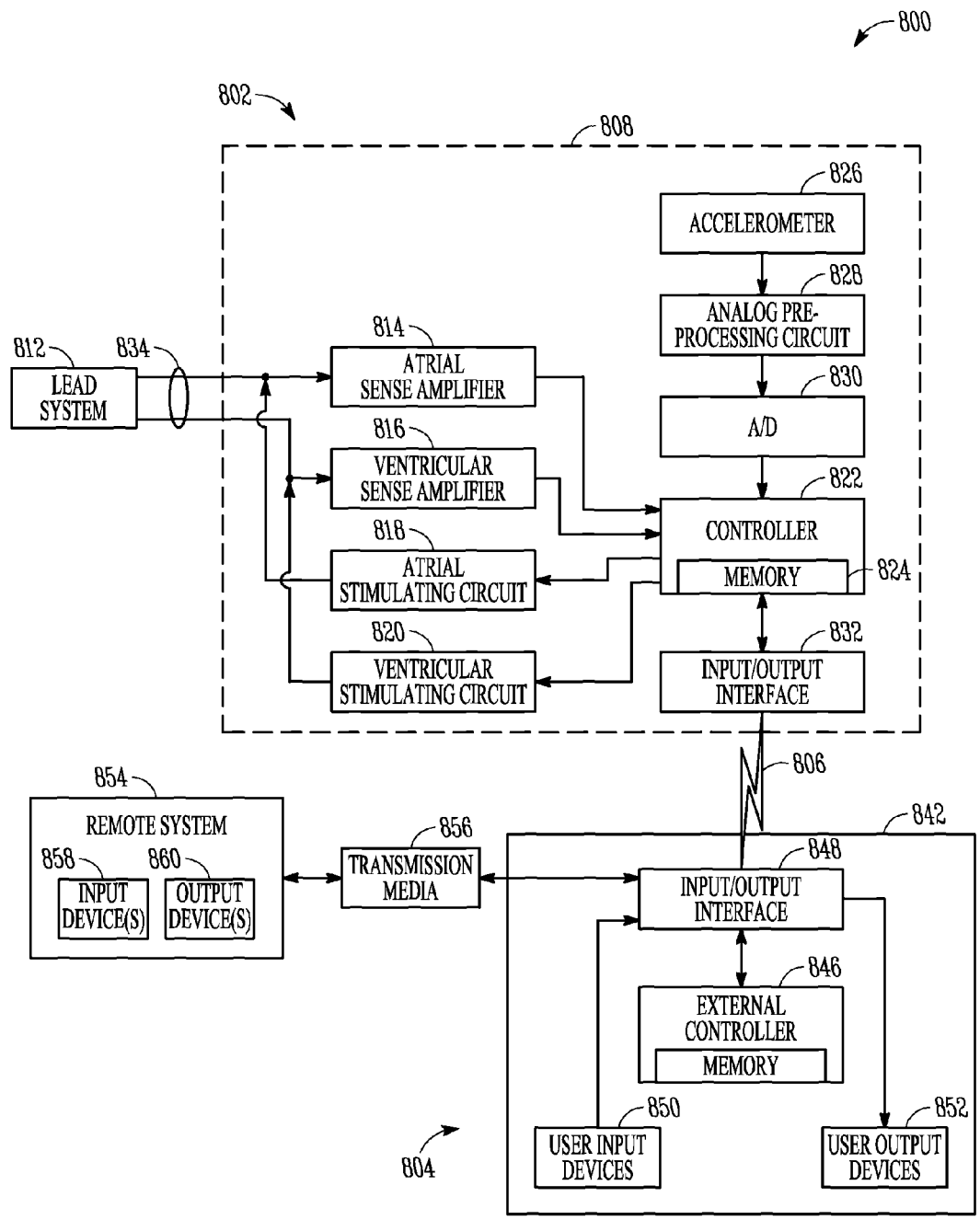
FIG. 8 depicts an exemplary system useful for detecting heart sounds, and executing any of the schemes and methods disclosed herein.

FIG. 8 depicts an exemplary system useful for detecting heart sounds, and executing any of the schemes and methods disclosed herein.

In FIG. 8, an exemplary system 800 for detecting and processing heart sounds includes an implantable system 802 and an external system 804. The implantable system 802 and external system 804 are configured to communicate via a communications link 806.

The implantable system 802 includes an implantable device 808 operatively coupled to a patient's heart by a lead system 812. The components of the implantable device 808 typically include an atrial sense amplifier 814, a ventricular sense amplifier 816, an atrial stimulating circuit 818, a ventricular stimulating circuit 820, a controller 822, a memory 824, an accelerometer 826, an analog pre-processing circuit 828, an analog-to-digital (A/D) converter 830, and an input/output (I/O) interface 832. The components of implantable device 808 are typically housed within an implantable housing (indicated by the broken lined box in FIG. 8), which may be implanted within the patient's chest cavity (e.g., in the pectoral region) or elsewhere.

The atrial sense amplifier 814, ventricular sense amplifier 816, atrial stimulating circuit 818 and ventricular stimulating circuit 820 are typically operatively coupled to the lead system 812 via a pair of conductors 834. The lead system 812 may include an atrial sensing electrode and an atrial stimulating electrode adapted to be disposed in the right atrial chamber of heart and a ventricular sensing electrode and a ventricular stimulating electrode adapted to be disposed in the right ventricular chamber of the heart.

Sensed atrial and ventricular electrical signals generated by the sensing electrodes are received by the atrial and ventricular sense amplifiers 814 and 816, respectively. Similarly, atrial and ventricular stimulating signals generated by the atrial and ventricular stimulating circuits 818 and 820 are applied to the atrial and ventricular stimulating electrodes, respectively. The atrial sense amplifier 814, ventricular sense amplifier 816, atrial stimulating circuit 818, and ventricular stimulating circuit 820, are each also operatively coupled to the controller 822.

In other embodiments, other sensing electrode configurations are used for internally sensing one or more electrical signals of the heart. In one example, only one sensing electrode may be used. Alternatively, one or more electrodes placed within the body but outside of the heart are used for sensing cardiac electrical signals. In yet another example, a sensing electrode is placed on the implantable housing. In each of these examples, the sensing electrodes are operatively coupled to the controller 822.

In the embodiment shown in FIG. 8, the sensing electrodes and the stimulating electrodes are disposed in association with the right side of heart. In other embodiments, one or more sensing electrode(s) and one or more stimulating electrode(s) are disposed in association with the left side of the heart (in lieu of being disposed in association with the right side of the heart, or in addition to sensing electrode(s) and stimulating electrode(s) disposed in association with the right side of the heart). The addition of left heart sensing may advantageously allow for the resolution of ambiguities due to disassociation of right and left heart conduction.

The controller 822 includes a microcontroller or microprocessor which is configured to execute a program stored in a read-only memory (ROM) portion of a memory unit 824, and to read and write data to and from a random access memory (RAM) portion of the memory unit 824. By executing the program stored in memory 824, the controller 822 is configured to process the atrial and ventricular electrical signals from the atrial and ventricular sense amplifiers 814 and 816, and to provide control signals to the atrial and ventricular stimulating circuits 818 and 820. In response, the stimulating circuits 818 and 820 provide stimulating pulses to the heart via atrial and ventricular stimulating electrodes at appropriate times. In other embodiments, the controller 822 may include other types of control logic elements or circuitry.

The implantable device 808 may be referred to as a dual-chamber pacemaker since pacemaking functions are provided to both atrial and ventricular chambers of the heart. In another embodiment, the implantable system includes a single-chamber pacemaker that senses electrical signals and provides stimulating pulses to a single chamber of the heart. In yet another embodiment, the implantable system does not provide any stimulation of heart tissues, but includes one or more sensing electrodes for sensing one or more electrical signals of the heart, and for providing corresponding sensed signals to controller 822. In still another embodiment, the implantable system does not provide any sensing electrodes for sensing any cardiac electrical signals, but is configured to sense signals representing heart sounds using a sensor such as the accelerometer 826, as described below, and to transmit information about such heart sounds from the implantable device 808.

In this description, the implantable device 808 is described as a dual-chamber pacemaker for the sake of illustration. It is to be understood, however, that implantable system 802 need not provide the stimulation functions described herein, and may provide other functions which are not described herein.

In some embodiments, a minute ventilation output channel and a minute ventilation input channel may be included. The minute ventilation output channel generates a test signal that is applied to a portion of the patient's thorax. An input channel receives and conditions a responsive signal. The content of the conditioned signal reveals respiration information.

An accelerometer 826 may be configured to provide sensed signals to the analog pre-processing circuit 828, which generates an analog output signal which is digitized by A/D converter 830. The digitized accelerometer signal is received by the controller 822. In the embodiment of FIG. 8, the accelerometer 826 is located within the housing of implantable device 808. In another embodiment, the accelerometer 826 is located on the housing of the implantable device. The accelerometer 826 may include, for example, a piezo-electric crystal accelerometer sensor of the type used by pacemakers to sense the level of physical activity of the patient, or may include other types of accelerometers. To detect heart sounds, this or other types of sound-detecting sensors or microphones may also be used, such as a pressure sensor or a vibration sensor configured to respond to sounds made by the heart.

In another embodiment, the system 800 includes two or more sound-detecting sensors. In such an embodiment, the plurality of sensed heart sound signals from the plurality of sensors may be individually transmitted to external system 804 for display as individual traces, may be combined (e.g., averaged) by external system 804 before being displayed as a single trace, or may be combined by controller 822 before being transmitted to external system 804 as a single heart sound signal. These sensors may include different types of sensors, sensors that are located in different locations, or sensors that generate sensed signals which receive different forms of signal processing.

In one embodiment, the accelerometer 826 is configured to generate sensed signals representative of two distinct physical parameters: (1) the level of activity of the patient; and (2) the heart sounds generated by heart. Accordingly, the analog pre-processing circuit 828 is configured to pre-process the sensed signals from the accelerometer 826 in a manner which conforms to the signal characteristics of both of these physical parameters. For example, if the frequencies of interest for measuring the patient's level of activity are typically below 10 Hz, while the frequencies of interest for detecting heart sounds are typically between 0.05 Hz and 50 Hz, then analog pre-processing circuit 828 may include a low-pass filter having a cutoff frequency of 50 Hz. The controller 822 may then perform additional filtering in software, as described above with reference to FIGS. 2-4, for example. Along with filtering, analog pre-processing circuit 828 may perform other processing functions including automatic gain control (AGC) functions.

The analog pre-processing circuit 828, analog-to-digital converter 830 and controller 822 may operate together to acquire, measure, and isolate heart sounds, such as S1, S2, S3, and S4 heart sounds, as described in "METHOD AND APPARATUS FOR THIRD HEART SOUND DETECTION," U.S. application Ser. No. 10/746,853, filed Dec. 24, 2003, which is hereby incorporated by reference for all it discloses. Alternatively, the analog pre-processing circuit 828 may simply provide automatic gain control functionality.

In some embodiments, the controller 822 performs one or more of steps the depicted and described with reference to FIGS. 3, 5, 6, and 7. Instructions for performing the operations of the aforementioned Figures may be stored in the memory device 824, for example. Additionally, any of the operations discussed and depicted with reference to FIGS. 3, 5, 6, and 7 may be performed cooperatively by the controller 822 within the implantable device 808 and another controller. For example, the controller 822 in the implantable device 808 may perform some of the operations, communicate needed results (via communications link 806, for example) to an external controller (contained in a programmer, for example), which may perform the remaining operations, and which may communicate results to either another external device or to the implantable device 802.

In another embodiment, the implantable device 808 has two pre-processing channels for receiving sensed signals from accelerometer 826. In still another embodiment, implantable device 808 includes two accelerometers, with one accelerometer configured to generate sensed signals representative of the level of activity of the patient and the other accelerometer configured to generate sensed signals representative of heart sounds. In these latter two embodiments, any hardware and/or software processing performed on the sensed signals can conform to the specific characteristics of the respective sensed signals. For example, the analog pre-processing circuit used for the level-of-activity sensed signals can provide a low-pass filter with a cutoff frequency of 10 Hz, while the analog preprocessing circuit for the heart-sound sensed signals can provide a band-pass filter with cutoff frequencies of 0.05 and 50 Hz. In the latter case, each accelerometer can be selected, located and/or oriented to maximize the detection of the respective physical parameter. In yet another embodiment, if the implantable device does not need to sense the level of activity of the patient, the accelerometer 826 may measure only the sounds made by heart. In yet another embodiment, an accelerometer for sensing heart sounds may be located at the distal end of a lead. In such an embodiment, the implantable device 802 may include an internal accelerometer (such as accelerometer 826) for detection of the patient's motion-based activity level.

The implantable device 802 may include or communicate with a pressure sensor that may be adapted for placement in the pulmonary artery or right ventricle, for example. Data from the pressure sensor may be relayed to the controller 822 via an analog pre-processing circuit and analog-to-digital converter, in a manner analogous to conveyance of accelerometer data, for example. Such data may be used to determine a preload patient's preload level, as discussed with reference to known variations of the method of FIG. 3, for example.

The controller 822 is capable of bi-directional communications with an external system 804 via an I/O interface 832. In one embodiment, the I/O interface 832 communicates using RF signals, which may be understood to include inductive coupling. In other embodiments, the I/O interface 832 communicates using optical signals, or a combination of RF and optical signals (e.g., RF signals for receiving data from the external system 804 and optical signals for transmitting data to external system 804, or vice-versa). The controller 822 uses the I/O interface 832 for bi-directional communications with the external system 804 to support conventional monitoring, diagnostic and configuration pacemaker functions. The controller 822 may also use the I/O interface 832 to telemeter data representative of the heart sounds sensed by accelerometer 826 to the external system 804. In various embodiments, the controller 822 further uses the I/O interface 832 to telemeter data representative of cardiac electrical signals (i.e., electrogram or EGM signals), which may include data representative of atrial electrical signals, sensed by the atrial sensing electrode, and/or data representative of ventricular electrical signals, sensed by the ventricular sensing electrode. Thus, implantable system 802 is capable of sensing heart sounds, atrial electrical signals and ventricular electrical signals, and of telemetering data representative of the heart sounds and/or cardiac electrical signals to external system 804. In other embodiments, the controller 822 telemeters data representative of cardiac electrical signals which were sensed by other configurations of internal cardiac sensing electrodes.

The external system 804 may include an external device 842. The external device 842 may include an external controller 846, an I/O interface 848, user input device(s) 850, and user output device(s) 852. Using the I/O interface 848, the external controller 846 is configured for bi-directional communications with the implantable device 808, for receiving input signals from input device(s) 850, and for applying control signals to output device(s) 852. The input device(s) 850 include at least one input device which allows a user (e.g., a physician, nurse, medical technician, etc.) to generate input signals to control the operation of external device 842, such as at least one user-actuatable switch, knob, keyboard, pointing device (e.g., mouse), touch-screen, voice-recognition circuit, etc. The output device(s) 852 include at least one display device (e.g., CRT, flat-panel display, etc.), audio device (e.g., speaker, headphone), or other output device which generates user-perceivable outputs (e.g., visual displays, sounds, etc.) in response to control signals. The external controller 846 may be configured to receive the data representative of heart sounds, atrial electrical signals and/or ventricular electrical signals from implantable system 802, and to generate control signals that, when applied to output device(s) 852, cause the output device(s) to generate outputs that are representative of the heart sounds, the atrial electrical signals and/or the ventricular electrical signals.

In one embodiment, the system 800 further includes a remote system 854 operatively coupled to communicate with the external system 804 via transmission media 856. The remote system 854 includes one or more user input device(s) 858, and one or more user output device(s) 860, which allow a remote user to interact with remote system 854. The transmission media 856 includes, for example, a telephone line, electrical or optical cable, RF interface, satellite link, local area network (LAN), wide area network (WAN) such as the Internet, etc. The remote system 854 cooperates with external system 804 to allow a user located at a remote location to perform any of the diagnostic or monitoring functions that may be performed by a user located at external system 804. For example, data representative of heart sounds and/or cardiac electrical signals are communicated by the external system 804 to the remote system 854 via the transmission media 856 to provide a visual display and/or an audio output on the output device(s) 860, thereby allowing a physician at the remote location to aid in the diagnosis of a patient. In various examples, the system 854 may be located in another room, another floor, another building, another city or other geographic entity, across a body of water, at another altitude, etc., from the external system 804.

The I/O interface 832 may establish a communication link with a communication device in physical proximity to the patient. For example, the I/O interface may establish a data link with a personal digital assistant, and may upload or download any of the data mentioned previously or hereafter. The personal digital assistant may, in turn, establish a link with an access point, so that the link may be effectively extended over a network, such as the Internet.

Embodiments of the invention may be implemented in one or a combination of hardware, firmware, and software. Embodiments of the invention may also be implemented as instructions stored on a machine-readable medium, which may be read and executed by at least one processor to perform the operations described herein. A machine-readable medium may include any mechanism for storing or transmitting information in a form readable by a machine (e.g., a computer). For example, a machine-readable medium may include read-only memory (ROM), random-access memory (RAM), magnetic disc storage media, optical storage media, flash-memory devices, electrical, optical, acoustical or other form of propagated signals (e.g., carrier waves, infrared signals, digital signals, etc.), and others.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims.

In the foregoing detailed description, various features are occasionally grouped together in a single embodiment for the purpose of streamlining the disclosure. This method of disclosure is not to be interpreted as reflecting an intention that the claimed embodiments of the subject matter require more features than are expressly recited in each claim. Rather, as the following claims reflect, inventive subject matter lies in less than all features of a single disclosed embodiment. Thus, the following claims are hereby incorporated into the detailed description, with each claim standing on its own as a separate embodiment.

What is claimed is:

1. A system comprising:
    an ambulatory device including:
        a transducer; and
        a control circuit coupled to the transducer, the control circuit configured to:
            monitor an S1 heart sound amplitude emitted by a heart of a patient;
            monitor a proxy variable indicating preload exhibited by the heart, the proxy variable including at least one of a heart sound amplitude or a blood pressure magnitude;
            measure a first inotropic state defined by a state variable pair obtained during a first time period, the state variable pair comprising: (1) an S1 heart sound amplitude value; and (2) a proxy variable value;
            measure a second inotropic state defined by a state variable pair obtained during a second time period, the state variable pair comprising: (1) an S1 heart sound amplitude value; and (2) a proxy variable value; and
            determine whether the heart has exhibited an inotropic state change by comparing the state variable pair of the second inotropic state to the state variable pair of the first inotropic state.

2. The system of claim 1, wherein the control circuit is configured to communicate a control signal to a device using information about the determined inotropic state change.

3. The system of claim 1 comprising a preload altering device, wherein the control circuit is configured to communicate a control signal to the preload altering device using information about the determined inotropic state change.

4. The system of claim 3, wherein the preload altering device includes a substance dispenser configured to deliver a substance to the patient.

5. The system of claim 4, wherein the substance is configured to alter a fluid status of the patient.

6. The system of claim 1 comprising an inotropic state altering device, wherein the control circuit is configured to communicate a control signal to the inotropic state altering device using information about the determined inotropic state change.

7. The system of claim 1, wherein the control circuit monitors a proxy variable indicating preload by monitoring an S3 heart sound.

8. The system of claim 1, wherein the control circuit monitors a proxy variable indicating preload by monitoring an S4 heart sound.

9. The system of claim 1, wherein the control circuit monitors a proxy variable indicating preload by: sensing a plurality of S3 or S4 heart sounds emitted by a heart of a patient, each of which is represented as a time-varying signal with at least one maxima and minima; and finding a greatest difference between a minima and maxima that are consecutive for each of the time-varying signals representing the plurality of S3 or S4 heart sounds, yielding a set of peak-to-peak differences; and
    wherein the control circuit monitors an inotropic state of the heart, using the set of peak-to-peak differences and an indicator of stroke volume.

10. The system of claim 1, wherein the ambulatory device includes a pressure sensor in data communication with the control circuit, and wherein the control circuit monitors a proxy variable indicating preload by monitoring blood pressure.

11. The system of claim 10, wherein the pressure sensor is configured to be located in a right ventricle.

12. The system of claim 10, wherein the pressure sensor is configured to be located in a pulmonary artery.

13. The system of claim 1, wherein the control circuit is configured to determine that the heart has exhibited an inotropic state change by identifying an occurrence in which the S1 heart sound indicates a change in stroke volume and the proxy variable indicates a change in preload.

14. The system of claim 13, wherein the S1 heart sound indicates an elevation in stroke volume and the proxy variable indicates a decline in preload.

15. The system of claim 13, wherein the S1 heart sound indicates a decline in stroke volume and the proxy variable indicates an elevation in preload.

16. The system of claim 1, wherein the ambulatory device comprises:
   stimulation and sensing circuitry interposed between the control circuit and an electrode system configured to make electrical contact with the heart; and
   wherein the control circuit is configured to apply cardiac resynchronization therapy to the heart, based upon a set of parameters.

17. The system of claim 16, wherein the control circuit is configured to adjust one or more of the set of parameters based upon the inotropic state or preload level exhibited by the heart.

18. The system of claim 1, wherein:
   the ambulatory device comprises an activity sensor coupled to the control circuit, the activity sensor generating a signal exhibiting a time-varying characteristic indicating an activity level of the patient; and
   the control circuit is configured to determine ventricular function, based upon the S1 heart sound, the proxy variable, and the signal generated by the activity sensor.

19. A system comprising:
   a preload altering device; and
   an ambulatory device including:
      a transducer; and
      a control circuit coupled to the transducer, the control circuit configured to:
         monitor an S1 heart sound amplitude emitted by a heart of a patient;
         monitor a proxy variable indicating preload exhibited by the heart, the proxy variable including at least one of a heart sound amplitude or a blood pressure magnitude;
         measure a first inotropic state defined by a state variable pair obtained during a first time period, the state variable pair comprising: (1) an S1 heart sound amplitude value; and (2) a proxy variable value;
         measure a second inotropic state defined by a state variable pair obtained during a second time period, the state variable pair comprising: (1) an S1 heart sound amplitude value; and (2) a proxy variable value; and
         determine whether the heart has exhibited an inotropic state change by comparing the state variable pair of the second inotropic state to the state variable pair of the first inotropic state; and
         communicate a control signal to the preload altering device using information about the determined inotropic state change;
   wherein the control circuit monitors a proxy variable indicating preload by:
      monitoring an S3 or S4 heart sound or a blood pressure; or
      sensing a plurality of S3 or S4 heart sounds emitted by a heart of a patient, each of which is represented as a time-varying signal with at least one maxima and minima; and finding a greatest difference between a minima and maxima that are consecutive for each of the time-varying signals representing the plurality of S3 or S4 heart sounds, yielding a set of peak-to-peak differences; and
   wherein the control circuit monitors an inotropic state of the heart, using the set of peak-to-peak differences and an indicator of stroke volume.

20. A system comprising:
   an inotropic state altering device; and
   an ambulatory device including:
      a transducer; and
      a control circuit coupled to the transducer, the control circuit configured to:
         monitor an S1 heart sound amplitude emitted by a heart of a patient;
         monitor a proxy variable indicating preload exhibited by the heart, the proxy variable including at least one of a heart sound amplitude or a blood pressure magnitude;
         measure a first inotropic state defined by a state variable pair obtained during a first time period, the state variable pair comprising: (1) an S1 heart sound amplitude value; and (2) a proxy variable value;
         measure a second inotropic state defined by a state variable pair obtained during a second time period, the state variable pair comprising: (1) an S1 heart sound amplitude value; and (2) a proxy variable value; and
         determine whether the heart has exhibited an inotropic state change by comparing the state variable pair of the second inotropic state to the state variable pair of the first inotropic state; and
         communicate a control signal to the inotropic state altering device using information about the determined inotropic state change;
   wherein the control circuit monitors a proxy variable indicating preload by:
      monitoring an S3 or S4 heart sound or a blood pressure; or
      sensing a plurality of S3 or S4 heart sounds emitted by a heart of a patient, each of which is represented as a time-varying signal with at least one maxima and minima; and finding a greatest difference between a minima and maxima that are consecutive for each of the time-varying signals representing the plurality of S3 or S4 heart sounds, yielding a set of peak-to-peak differences; and
   wherein the control circuit monitors an inotropic state of the heart, using the set of peak-to-peak differences and an indicator of stroke volume.

* * * * *